US009121856B2

(12) United States Patent
Stills, Jr. et al.

(10) Patent No.: US 9,121,856 B2
(45) Date of Patent: Sep. 1, 2015

(54) **METHOD AND SYSTEM FOR DIAGNOSIS OF *LAWSONIA INTRACELLULARIS***

(71) Applicant: University of Kentucky Research Foundation, Lexington, KY (US)

(72) Inventors: Harold F. Stills, Jr., Lexington, KY (US); David W. Horohov, Lexington, KY (US); Allen E. Page, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/676,898

(22) Filed: Nov. 14, 2012

(65) Prior Publication Data

US 2013/0164765 A1 Jun. 27, 2013

Related U.S. Application Data

(60) Provisional application No. 61/560,275, filed on Nov. 15, 2011.

(51) Int. Cl.
*G01N 33/554* (2006.01)
*G01N 33/569* (2006.01)
*G01N 33/53* (2006.01)
*G01N 33/68* (2006.01)

(52) U.S. Cl.
CPC ...... *G01N 33/6893* (2013.01); *G01N 33/56911* (2013.01); *G01N 2469/20* (2013.01)

(58) Field of Classification Search
CPC .................... G01N 33/56911; G01N 2469/20; C12Q 1/689; C07K 14/195
See application file for complete search history.

(56) References Cited

U.S. PATENT DOCUMENTS 7,029,683 B1 * 4/2006 Panaccio et al. ........... 424/234.1
2006/0024696 A1 * 2/2006 Kapur et al. ...................... 435/6

OTHER PUBLICATIONS

Ion Exchange Chromatography (IEC), http://www.proteinchemist.com/tutorial/iec.html, accessed Jan. 28, 2014.*

Bollag, Ion-Exchange Chromatography (Chapter 2), Methods in Molecular Biology, 1995; 36: 11-22.* http://www.gelifesciences.com/webapp/wcs/stores/servlet/productByld/en/GELifeSciences/17070901; accessed Mar. 25, 2014.*

Boesen, H.T., Jensen, T.K., Brees, D.J., Sondhoff, A.H., Kluge, J.P., Andreasen, C.B. And Brown, C. M. (2005) Evaluation of a novel enzyme-linked immunosorbent assay for serological diagnosis of porcine proliferative enteropathy. Vet. Microbiol. 109, 105-112.

Guedes, R.M., Gebhart, C.J., Guedes, R.M., Gebhart, C.J., Deen, J. And Winkelman, N.L. (2002a) Serologic follow-up of a repopulated swine herd after an outbreak of proliferative hemorrhagic enteropathy. Can. J. vet. Res. 66, 258-263.

Guedes, R.M., Gebhart, C.J., Herbst, W., Hertrampf, B., Schmitt, T., Weiss, R. And Baljer, G. (2002b) Validation of an immunoperoxidase monolayer assay as a serologic test for porcine proliferative enteropathy. J. vet. Diag. Invest. 14, 528- 530.

Jacobson, M., Aspan, A., Jones, G.F., Ward, G.E., Murtaugh, M.P., Lin, G. And Gebhart, C.J. (2004) Routine diagnostics of Lawsonia intracellularis performed by PCR, serological and post mortem examination, with special emphasis on sample preparation methods for PCR. Vet. Microbiol. 102, 189-201.

Kroll, J.J., Eichmeyer, M.A., Lavoie, J.P., Drolet, R., Parsons, D., Leguillette, R., Sauvageau, R., Shapiro, J., Houle, L., Halle, G., Gebhart, C.J. (2005) Lipopolysaccharide-based enzyme-linked immunosorbent assay for experimental use in detection of antibodies to Lawsonia intracellularis in pigs. Clin. Diagn. Lab. Immunol. 12, 693-699.

Page, A.E., Slovis, N.M., Gebhart, C.J., Wolfsdorf, K., Mapes, S.M. And Pusterla, N. (2011b) Serial use of serologic assays and fecal PCR assays to aid in identification of subclinical Lawsonia intracellularis infection for targeted treatment of Thoroughbred foals and weanlings. J. Am. Vet. Med. Assoc. 238, 1482-1489.

Page, A.E., Stills, H.F., Chander, Y., Gebhart, C.J., Horohov, D.W. (2011) Adaptation and validation of a bacteria-specific enzyme-linked immunosorbent assay for determination of farm-specific Lawsonia intracellularis seroprevalence in central Kentucky Thoroughbreds. Equine Veterinary Journal 43 (Suppl. 40) 25-31.

Pusterla, N., Higgins, J.C. et al. (2008a) Epidemiological survey on farms with documented occurrence of equine proliferative enteropathy due to Lawsonia intracellularis. Vet. Rec. 163, 156-158.

Sorensen, K. And Brodbeck, U. (1986) Assessment of coating-efficiency in ELISA plates by direct protein determination. J. Immunol. Methods 95, 291-293.

Watarai, M., Yamato, Y. et al. (2004) Enzyme-linked immunosorbent assay to detect Lawsonia intracellularis in rabbits with proliferative enteropathy. J. vet. med. Sci. 66, 735-737.

(Continued)

*Primary Examiner* — Gary Nickol
*Assistant Examiner* — Lakia Tongue
(74) *Attorney, Agent, or Firm* — Stites & Harbison PLLC; Mandy Wilson Decker

(57) ABSTRACT

A method, system, and kit are provided for diagnosing *L. intracellularis* infection or exposure in a subject. The method includes purifying whole *L. intracellularis* from host cells and host debris produced in or on a suitable medium and adhering the purified whole *L. intracellularis* on a suitable material to form an antigen substrate for determining whether a subject produces *L. intracellularis*-specific antibodies against the antigen to thereby indicate *L. intracellularis* exposure or infection in the subject. The kit includes purified whole *L. intracellularis* produced from host cells and host debris adhered to a suitable material to form an antigen substrate adapted for screening serum from a subject. A method for diagnosing *L. intracellularis* exposure or infection in a subject includes acquiring a serum sample from a subject, introducing the serum sample to an antigen substrate followed by detecting a presence of *L. intracellularis*-specific antibodies in the serum.

9 Claims, 5 Drawing Sheets

(56) References Cited

OTHER PUBLICATIONS

Wattanaphansak, S., Asawakarn, T. et al. (2008) Development and validation of an enzyme-linked immunosorbent assay for the diagnosis of porcine proliferative enteropathy. J. vet. Diagn. Invest. 20, 170-177.

* cited by examiner

METHOD AND SYSTEM FOR DIAGNOSIS OF *LAWSONIA INTRACELLULARIS*

CROSS REFERENCE TO RELATED APPLICATIONS

This application claims the benefit of Provisional Application Ser. No. 61/560,275, filed Nov. 15, 2011 herein incorporated by reference.

FIELD OF THE INVENTION

The presently-disclosed subject matter relates to methods and systems for use in the diagnosis of *Lawsonia intracellularis* infection in a subject. In particular, the presently-disclosed subject matter relates to an enzyme-linked immunoabsorbent assay (ELISA) for diagnosing *Lawsonia intracellularis* infection and exposure in a subject.

BACKGROUND OF THE INVENTION

Exposure to pathogens cause illness and even death to living organisms such as humans, animals and plants. There are numerous techniques used to diagnose pathogen infections and exposure.

One pathogen of importance to mammals is the bacterium, *L. intracellularis. L. intracellularis* is an obligate intracellular, Gram-negative rod, is the causative agent of proliferative enteropathy (Lawson and Gebhart 2000). *L. intracellularis* is viewed as an emerging cause of proliferative enteropathy in a variety of mammalian species (Drolet et al. 1996; Hotchkiss et al. 1996), including horses (Williams et al. 1996; Cooper et al. 1997; Frank et al. 1998; Brees et al. 1999), where the bacteria causes equine proliferative enteropathy (EPE).

Clinical signs of EPE, usually seen in weanlings or young yearlings (Frank et al. 1998; Brees et al. 1999; Lavoie et al. 2000; Schumacher et al. 2000; Frazer 2008), include anorexia, fever, lethargy, depression, peripheral edema caused by hypoproteinemia/hypoalbuminemia, weight loss, colic and diarrhea. In addition, thickened small intestine detected by abdominal ultrasound is considered highly suggestive of EPE when accompanied by compatible clinical signs. Commercially available ante mortem tests for EPE include fecal *L. intracellularis*-specific polymerase chain reaction (PCR) and the serum immunoperoxidase monolayer assay (IPMA), both of which have been adapted from their use in pigs where the tests are highly specific; sensitivity is reported to be high for the IPMA (Guedes et al. 2002a,b) but variable for faecal PCR (Herbst et al. 2003; Jacobson et al. 2004).

Although the epidemiology of EPE is uncertain, it is believed that transmission occurs through the ingestion of *L. intracellularis*-contaminated fecal material from wild or domestic animals (Pusterla et al. 2008b). While most cases of EPE typically occur in the fall and early winter (Frazer 2008; Page et al. 2011b), the reason for this seasonal predilection has not yet been determined. One possibility is the known susceptibility of weanlings to this infection and weaning typically occurs during this time of year (Frazer 2008). Another possibility would be that the environmental conditions at that time favor transmission by increasing exposure burdens.

Previous work on the detection of *L. intracellularis*-specific antibodies on specific farms demonstrated seroprevalences ranging from 33.8 to 45.5% on two California farms (Pusterla et al. 2008a) and up to 60% on a Kentucky farm (Page et al. 2011b), utilizing the IPMA method. A large scale, recent study, detailed within, found that seroprevalence on some equine farms actually approaches 100%.

Enzyme-linked immunosorbent assay (ELISA) for detection of *L. intracellularis*-specific antibodies have been previously developed for the pig and rabbit (Watarai et al. 2004; Boesen et al. 2005; Kroll et al. 2005; Wattanaphansak et al. 2008).

SUMMARY OF THE INVENTION

The present invention is directed to a novel method for detecting the presence of *Lawsonia intracellularis*-specific antibodies for the diagnosis of *Lawsonia intracellularis* exposure or infection. The present method and system may also be used for evaluating the efficacy of a vaccine. The presently disclosed subject matter overcomes sensitivity and specificity issues associated with prior techniques for evaluating *Lawsonia intracellularis* exposure and infection including those described above in the Background of the Invention section. The present method and system can be used for subjects including but not limited to farm animals, such as horses (including race horses) and swine.

One unique aspect of the present method and system for detecting *Lawsonia intracellularis* exposure or infection includes a process in which whole *L. intracellularis* cells, are purified for use as an antigen in the ELISA. As a result, the present method and system uses whole purified *Lawsonia intracellularis* in contrast to prior techniques which are directed to identifying the presence of a *Lawsonia intracellularis* amongst host cells and host cell debris due to a lack of complete purification of the *L. intracellularis*. In various specific forms of the present method and system, the purified *L. intracellularis*, e.g. bacteria, is a chromotography-purified whole *L. intracellularis*. As will be recognized by those of ordinary skill in the art, it can be useful to monitor a particular subject over time using the methods and systems described herein, i.e., conducting multiple diagnostic tests at different time points.

The present invention, in one form thereof, relates to a method for diagnosing *L. intracellularis* exposure or infection in a subject. The method includes acquiring a blood sample from a subject and processing that blood sample using centrifugation which separates serum from whole blood cells to form an isolated sample. The isolated sample is analyzed for the presence of *L. intracellularis*-specific antibodies using an ELISA and the subject is diagnosed as having a *L. intracellularis* infection or exposure if the presence of *L. intracellularis*-specific antibodies are detected when analyzing the isolated sample. For analysis of the isolated sample, *L. intracellularis* whole cells are processed and purified using centrifugation followed by chromatography.

The present invention, in another form thereof, relates to a method for evaluating effectiveness of a vaccine against a *L. intracellularis* infection in a subject. The method includes administering a test vaccine to a subject and subsequently acquiring a blood sample from the subject. The blood sample is processed using centrifugation which separates serum from whole blood cells form an isolated sample. The isolated sample is analyzed for presence of *L. intracellularis*-specific antibodies. The vaccine is determined to be effective at eliciting an immune response if *L. intracellularis*-specific antibodies are detected when analyzing the isolated sample and the subject does not exhibit symptoms of *L. intracellularis* infection or signs of clinical disease.

In one further specific form of the method for evaluating effectiveness of a vaccine, the method further includes exposing a subject to a *L. intracellularis* after the vaccine has been administered to the subject and the subject has had sufficient time to develop an immune response to the vaccine but before acquiring the blood sample from the subject. Effectiveness of the vaccine is determined if the subject blood sample has detectable amounts of *L. intracellularis*-specific antibodies and remains free of signs of clinical disease.

The present invention, in another form thereof, relates to a method for diagnosing *L. intracellularis* infection or exposure in a subject. The method includes purifying whole *L. intracellularis* from host cells and host debris produced in or on a suitable medium. The purified *L. intracellularis* is adhered on a suitable material to form an antigen substrate for determining whether a subject produces *L. intracellularis* specific-antibodies against the antigen and thereby indicate a *L. intracellularis* exposure or infection in the subject.

The pathogen may be purified from host cells and host debris using centrifugation followed by ion-exchange chromatography. The suitable material upon which the purified *L. intracellularis* is adhered may be an enzyme-linked immunosorbent assay (ELISA) plate. In one specific form, the method may include introducing a serum sample from a subject to the antigen substrate to determine whether the serum contains *L. intracellularis*-specific antibodies against the antigen. The serum may be produced from centrifugation of a blood sample taken from the subject.

The present invention, in another form thereof, relates to a kit for diagnosing pathogen infection or exposure in a subject. The kit includes purified, whole pathogen adhered to a suitable material to form an antigen substrate. The antigen substrate is adapted to be used to screen serum from a subject for *L. intracellularis*-specific antibodies against the antigen, to thereby indicate *L. intracellularis* exposure or infection in the subject. Advantageously, the purified *L. intracellularis* is produced by centrifugation of pathogen host cells and host debris followed by ion-exchange chromatography. Further, in one specific form, a suitable material is an ELISA plate.

The present invention, in another form thereof relates to a method for diagnosing *L. intracellularis* infection or exposure in a subject. The method included acquiring a serum sample from a subject and introducing the serum sample to an antigen substrate comprising purified *L. intracellularis* adhered to a suitable medium. The purified *L. intracellularis* is produced from host cells and host debris. Presence of *L. intracellularis*-specific antibodies are detected in the serum against the antigen substrate, thereby indicating pathogen exposure or infection in the subject.

Exemplary conditions and reagents that can be used in some embodiments of the present method and system include the ELISA methods disclosed herein. A carbonate buffer can be used as a coating buffer. The antigen can be provided at a concentration of about 2.5 micrograms/ml, and the plate/antigen can incubate overnight at about 4 degrees C. PBS with Tween can be used as the ELISA wash, and polyvinyl alcohol can be used as the blocking buffer. The sample serum dilution can be about 1:100, and the sample incubation can be at room temperature for about 1 hour. The antibodies can be mouse anti-horse conjugated with HRP, and the anti IgG incubation can be at room temperature for about 1 hour in the dark. In some embodiments anti-IgM can be used. The substrate can be TMB (3,3',5,5'-tetra-methylbenzidine). A standard curve can be generated from known IPMA titer, and ELISA units (EU) can be determined on a continuous scale, allowing for a sensitive and specific measurement. The ELISA procedure can be modified to incorporate other species-specific reagents such that the ELISA can test samples originating from a variety of other species including, but not limited to, swine, hamsters, rabbits, mice, rats, non-human primates, humans, raccoons, birds and insects. It is important to note that the present ELISA can be easily adapted for use in a variety of other species (i.e. not just horses), which will be readily apparent to those of ordinary skill in the art.

DETAILED DESCRIPTION

Figure 1:
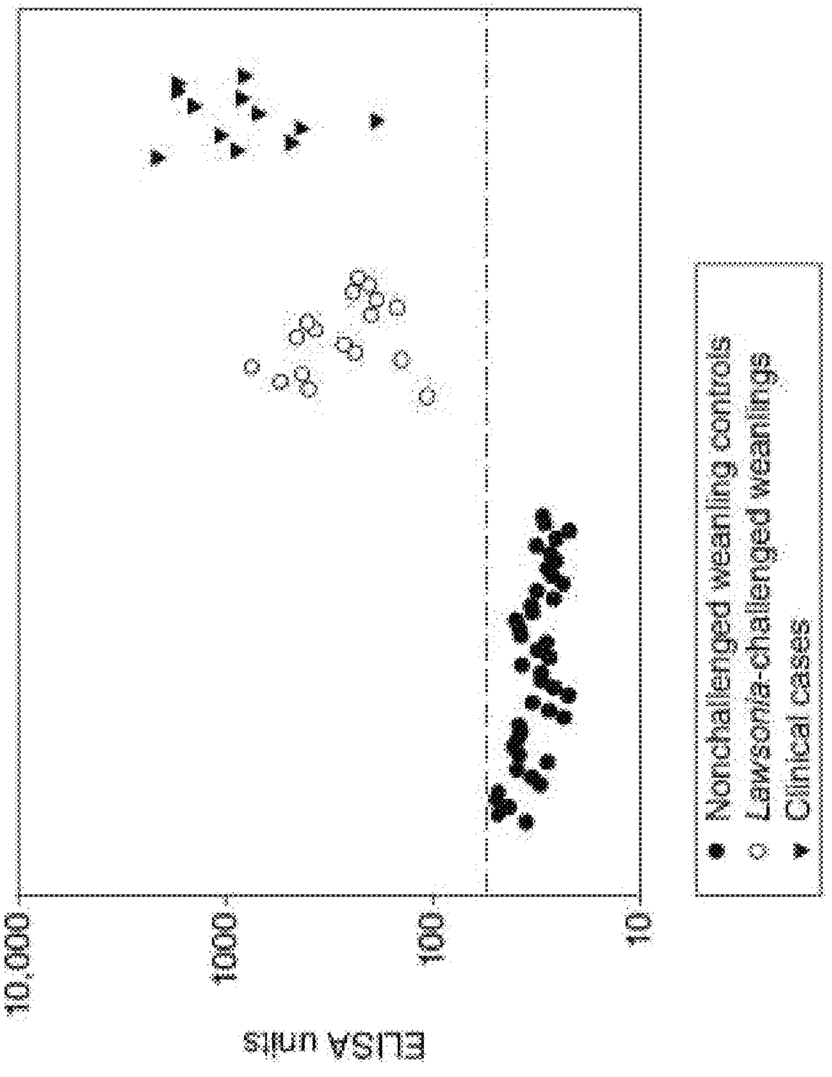
FIG. 1 is a plot relating enzyme-linked immunosorbent assay (ELISA) units (EU) values for nonchallenged weanling controls and *L. intracellularis*-challenged weanlings as well as clinical EPE cases in which dashed bar represents 55 EU, of the cut-off for positive samples.

The present method and system will now be described with reference to specific experiments demonstrating the efficacy of the present method and system in diagnosing *L. intracellularis* infection or exposure. However, the following examples and experiments do not limit the scope of the present disclosure and variations to the methods and experiments described below can be modified in accordance with the understanding of one of ordinary skill in the art.

Materials and Methods

Farm Selection and Information Gathering

A total of 25 Thoroughbred farms were recruited for participation in a study using various methods to test efficacy of the present methods. Farms provided information regarding EPE cases in the preceding 3 years. These data were used to classify farms as either having confirmed cases of EPE, suspected but unconfirmed cases of EPE, or no recent cases of EPE. Farms were considered to have had confirmed EPE cases if they had one or more weanlings with clinical signs compatible with EPE, hypoproteinaemia and hypoalbuminemia, and either a concurrent positive faecal PCR or serum IPMA titer result (1:60 or greater) in the preceding 3 years. For the purpose of this study, compatible clinical signs for EPE were anorexia, fever, lethargy, depression, dependent edema, rapid weight loss, colic and diarrhea. Farms were considered to have had suspected EPE cases if they had one or more weanlings with signs compatible with EPE, but neither a positive faecal PCR nor positive serum IPMA titer result (1:60 or greater). Farms were considered to have had no recent history of EPE if there were no horses with clinical signs of EPE within the preceding 3 years.

After the conclusion of the study, all participating farms were requested to complete a questionnaire regarding EPE cases on the farm during the study period. Based on this information, farms were classified for the study period into the 3 categories as above.

Study Period

The study period began Aug. 16, 2010 and concluded Jan. 5, 2011. For some farms, an optional sample collection period from 31 Jan. to 2 Feb. 2011 was included in the study due to a large increase in the number of seropositive samples in January. Samples were collected from the farms once during a 3 day period every 4 weeks.

Horses

Although some farms housed non-Thoroughbred horses, only Thoroughbred horses were included in the study. All horses in the study were born during the 2010 foaling season and weaned by November 2010. Farms were requested to provide a list of all 2010 horses present on the farm in early August 2010. If a farm had 14 or fewer 2010 horses at this time, all horses were included in the study. For those farms with 15 or more horses present in early August, 15 horses were chosen randomly to participate (except for Farm 19, from which all 16 horses were included in the study at the farm's request). Randomization was achieved by assigning each horse a sequential number and utilizing a random number generator (Microsoft Excel) to select the 15 horses for inclusion in the study. Each horse included in the study was assigned a unique 3 digit identification number for ease of results tracking, as well as maintaining anonymity.

Sample Collection and Handling

Once every 4 weeks, a 10 ml sample of whole blood was collected into individually labeled, sterile, red-top 10 ml blood tubes via jugular venipuncture. Samples were submitted and held at centralized laboratories at 4° C. for less than 24 h before they were collected and transported to the Maxwell H. Gluck Equine Research Center at the University of Kentucky. Upon arrival, samples were immediately centrifuged at 800×g for 10 min. Serum was transferred to tubes labeled with the month and a unique 3 digit code assigned to its horse and frozen at −20° C. until analyzed.

For various reasons, including public sale, private sale or a horse being returned to its owner, a number of blood samples were omitted from the study. As such, data from any horses that left the study prior to November were completely excluded from the data set. Horses remained in the study even if one or more samples were not collected after October.

Serum samples obtained from 6 *Lawsonia intracellularis*-challenged weanlings and 15 uninfected controls were included for the validation of the ELISA, with information regarding the challenge reported elsewhere (Page et al. 2011a).

*Lawsonia intracellularis*-Specific Immunoperoxidase Monolayer Assay

The IPMA method for determining *L. intracellularis*-specific antibody titers was performed as previously described (Guedes et al. 2002b).

Purification of *L. intracellularis*

*L. Intracellularis* is purified using centrifugation and ion-exchange chromatography. Generally speaking ion-exchange chromatography involves the process of separating polar (charged) materials (compounds, particulates, etc.) on the basis of the charges carried by solute molecules. Materials to be separated are adhered to the reversibly charged insoluble matrix of the exchange material and then sequentially eluted by altering either the solvent pH or ionic concentration. In this specific case DEAE serves as the ion exchange media to which the centrifuged bacteria is adhered and then purified by elution with increasing buffer salt (NaCl) concentrations. Specifically, the bacteria are initially isolated from cellular debris initially by low speed centrifugation (400-600×g) to remove cellular debris followed by high speed centrifugation (6,500×g) to pellet the bacteria. The bacteria, suspended in 0.01 M. Phosphate buffer, is applied to a low pressure liquid chromatography column (2.5 cm×30 cm) containing DEAE-Sepharose CL-6B equilibrated with 0.01 M. Phosphate buffer, pH 6.8. The column is washed with 5 volumes of 0.01 M. Phosphate buffer, pH 6.8. The buffer is then changed sequentially to 0.01 M. Phosphate buffer, pH 6.8 with 0.1 M NaCl, 0.01 M. Phosphate buffer, pH 6.8 with 0.15 M NaCl, and 0.01 M. Phosphate buffer, pH 6.8 with 0.2 M NaCl and the eluted protein peaks collected. The eluted material is concentrated by centrifugation (6,500 g for 60 minutes at 4° C.) if necessary and resuspended in PBS with 0.02% $NaN_3$.

Referring now to one specific purification process, porcine-origin *L. intracellularis* was obtained from cell culture (Lawson et al. 1993) and purified using diethylaminoethyl (DEAE) column chromatography, which allowed the bacterium to be eluted as a whole organism. The presence of *L. intracellularis* in the eluate was verified microscopically using Gimenez stain, in addition to PCR for *L. intracellularis*, as previously described (Jones et al. 1993). Additionally, no other bacteria were present following aerobic and anaerobic culture, as well as Gram staining. The pooled purified bacterial eluate with sodium azide was kept refrigerated (4° C.). Quantification of the purified bacterial protein performed using the bicinchoninic acid (BCA) method (Sorensen and Brodbeck 1986).

*Lawsonia intracellularis*-Specific Enzyme-Linked Immunosorbent Assay

The ELISA was based on previously described methods (Wattanaphansak et al. 2008) with respect to starting concentrations of reagents and a checkerboard titration scheme, as described elsewhere (Kroll et al. 2005; Wattanaphansak et al. 2008). Factors influencing background were minimized using previously described methods (Wattanaphansak et al. 2008). From this, it was found that serum dilutions of 1:100 produced the most consistent results with minimal background. Further, based on this approach, the optimum concentration of antigen was 2.5 μg/ml and the use of a polyvinyl alcohol block was superior to 5 or 10% skim milk.

The ELISA plates (Immunolon 1b Flat Bottom Microtiter plates) were coated with 2.5 μg/ml of purified *L. intracellularis* in carbonate buffer, then covered with Parafilm-M and allowed to sit overnight at 4° C. After plates incubated overnight, they were washed 3 times with phosphate-buffered saline with 0.05% Tween-20 (PBST) using an ELISA plate washer (MW 96/384). The coated plates were then blotted dry before adding 200 μl/well of blocking buffer (polyvinyl alcohol [Mowiol 6-98] 1% [w/v] in distilled water) for 1 hour at room temperature. After blocking, the plates were washed 3 times, as above. Sera were diluted at 1:100 in blocking buffer and added (100 μl) to duplicate wells. Plates were then incubated at room temperature for 1 h. Duplicate, serially diluted (1:60 through 1:3840) serum samples from a weanling exhibiting clinical signs compatible with EPE, including anorexia, weight loss and dependentedema, was used to generate a standard curve. This weanling tested positive repeatedly at 1:1920 using the IPMA method. Negative control samples included serum from repeatedly *L. intracellularis* antibody-negative weanlings along with a duplicate sample of 100 μl fetal equine serum diluted 1:100. After 1 h incubation with diluted test and control sera, the plate was washed 3 times and 100 ml of murine anti horse IgG (1:4000) conjugated with horseradish peroxidase (HRP) was added to each well. The plate was then incubated in the dark for 1 h at room temperature before being washed 3 times. To each well was then added 100 μl of 3,3',5,5'-tetra-methylbenzidine (TMB) solution (SureBlue TMB Microwell Peroxidase substrate) for 2 min before the reaction was stopped with TMB Stop solution.

Absorbance at 450 nm was read within 5 min using an ELISA plate reader (Benchmark plus). Results from the test sera were converted to ELISA units (EU) utilizing a linear trend line from the standard curve generated from each plate. A coefficient of determination ($r^2$) of ≥0.90 was required for the plate to be considered valid (Kroll et al. 2005).

A positive cut-off of 55 EU or greater was utilized based on nonchallenged weanlings having an average of 33 EU and a standard deviation of 7 EU (Page et al. 2011a); these samples repeatedly tested negative via IPMA. By setting the cut-off at 55 EU, this value is 3 s.d. units above the negative control averages and represents the upper limit of a 99% confidence interval.

Evaluation of Assay Repeatability

Twenty-four samples were selected for the ELISA repeatability test. These represented a variety of negative (<55 EU), low (55-119 EU), mid (120-239 EU) and high (~240 EU) samples. For intra-assay repeatability, 3 replicates of each sample were performed on the same plate. For inter-assay repeatability, 3 replicates of each sample were run on duplicate plates on different days. Coefficient of variation (CV=s.d./mean×100%) of the 3 replicates from each test were evaluated. In addition, CV's of the standard curve optical densities (ODs) from each plate was evaluated.

Data Analysis

Farms 8 and 9 were ultimately considered as one farm data set since the horses from these 2 farms were combined into one population once the foals were weaned. Likewise, Farms 22 and 23 were combined into one data set for the same reason.

One way analysis of variance (ANOVAs) (Holm-Sidak method) was used to evaluate differences in ELISA titers between farms categorized based on their past EPE status. Post hoc t tests were performed to evaluate the differences between groups. Chi-square analyses were used to assess seroprevalence results. Calculated P values≤0.05 were considered to be statistically significant.

Results

In order to validate our ELISA, serum samples of varying EU were run in triplicate with an overall intra-assay CV of 6.73 and inter-assay CV of 9.60. For the standard curve, CVs ranged from 2.08 to 7.69 with a mean of 4.85 and the most dilute sample (1:3840 dilution) had the highest CV. Additionally, ELISA analysis of serial serum samples from *L. intracellularis* challenged weanlings demonstrated seroconversion on or before Day 20 post challenge with all weanlings obtaining EU>120 and a maximum of 746 EU while all nonchallenged weanlings remained below 55 EU (Page et al. 2011a).

Figure 2:
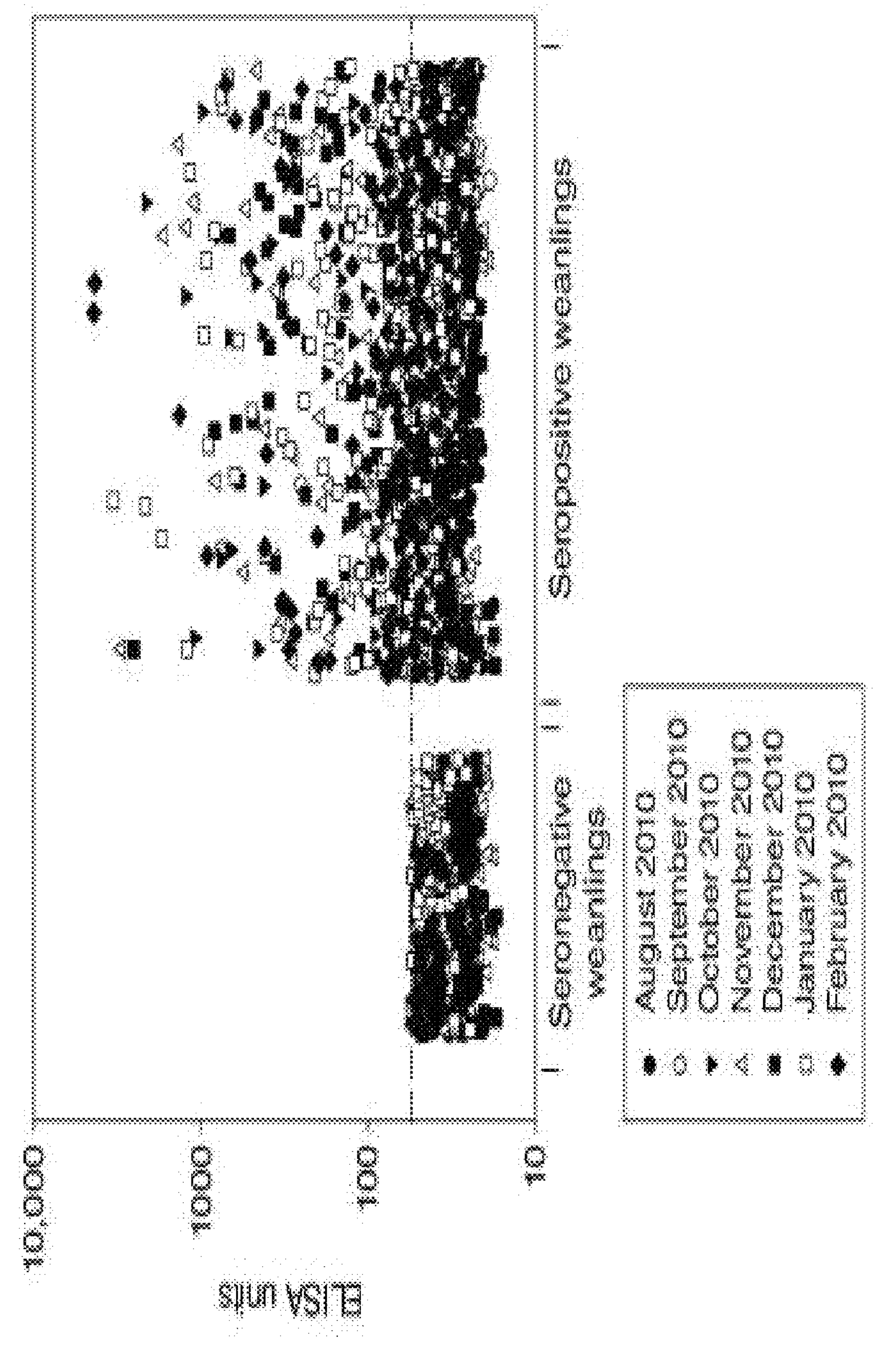
FIG. 2 is a plot relating ELISA units to weanlings over time in which all studied time points from those weanlings remained seronegative (<55 Enzyme-linked immunosorbent assay (ELISA) units (EU) for the entire study and those that seroconverted at any point≥55 EU) during the study period. Each column for the study horses represents an individual horse. Dashed bar represents 55 EU.

Provided in FIG. 1 are EU results for nonchallenged controls and experimentally challenged weanlings (Page et al. 2011a), as well as clinically affected field cases from the study period (EU values shown are those found at the initial time of clinical presentation). Weanlings with clinical EPE had similar and, in some cases greater, serum antibody levels against *L. intracellularis* when compared with experimentally challenged weanlings. FIG. 2 includes EU results from all horses in the present study divided into 2 groups; study horses that failed to seroconvert (<55 EU) during the study and study horses that seroconverted (≥55 EU) at any point during the study period but failed to show clinical signs of EPE. A number of the nonclinical, seropositive horses exhibited very high EU.

Figure 3:
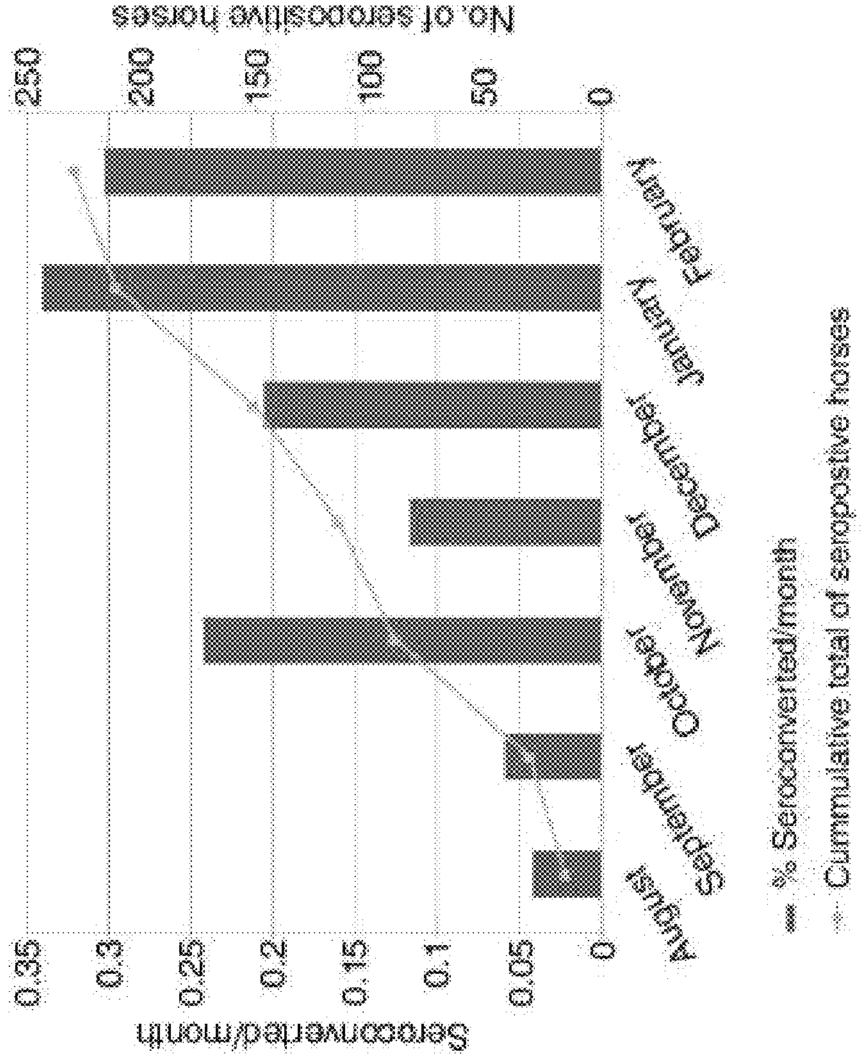
FIG. 3 is a graph depicting monthly percentage of previously seronegative horses that seroconverted (55 Enzyme-linked immunosorbent assay (ELISA) units ((EU) or greater) during a given month and total number of seropositive horses.

Overall, a total of 337 horses were included in the seroprevalence data set as they were present on the farms through at least November 2010. Of these 337 horses, a total of 229 horses or 68.0% of the study population, tested positive (≥55 EU) for *L. intracellularis*-specific antibodies via the ELISA at one or more time points. The monthly percentage of previously seronegative horses that seroconverted during a given month and the accruing totals are shown in FIG. 3. Overall, there was a steady increase in the number of seropositive horses over time

TABLE 1

Seroprevalence by farm according to previous EPE history and equine proliferative enteropathy (EPE) status during the study period

| Farm | History of previous EPE cases | 2010 foaling season EPE cases | Total ELISA positive horses | Total No. horses sampled | Seroprevalence |
|---|---|---|---|---|---|
| 1 | No | No | 11 | 15 | 73.3% |
| 2 | Suspected | No | 3 | 15 | 20.0% |
| 3 | Confirmed | Confirmed | 9 | 9 | 100.0% |
| 4 | Confirmed | No | 7 | 12 | 58.3% |
| 5 | Confirmed | No | 10 | 15 | 68.7% |
| 6 | Confirmed | Confirmed | 9 | 10 | 90.0% |
| 7 | No | No | 2 | 14 | 14.3% |
| 8 and 9 | Confirmed | No | 16 | 26 | 61.5% |
| 10 | Confirmed | Confirmed | 9 | 15 | 60.0% |
| 11 | No | No | 10 | 15 | 66.7% |
| 12 | Confirmed | No | 5 | 9 | 55.6% |
| 13 | Suspected | Confirmed | 13 | 15 | 86.7% |
| 14 | Confirmed | No | 9 | 15 | 60.0% |
| 15 | Suspected | No | 9 | 15 | 60.0% |
| 16 | Confirmed | Confirmed | 11 | 11 | 100.0% |
| 17 | Confirmed | Confirmed | 14 | 15 | 93.3% |
| 18 | Confirmed | No | 15 | 15 | 100.0% |
| 19 | Confirmed | No | 12 | 16 | 75.0% |
| 20 | No | No | 2 | 7 | 28.6% |
| 21 | Confirmed | Confirmed | 11 | 14 | 78.6% |
| 22 and 23 | Confirmed | Confirmed | 24 | 29 | 82.8% |
| 24 | No | No | 10 | 15 | 66.7% |
| 25 | No | No | 8 | 15 | 53.5% |

Farm specific seroprevalences ranged from 14.3-100%

Figure 4:
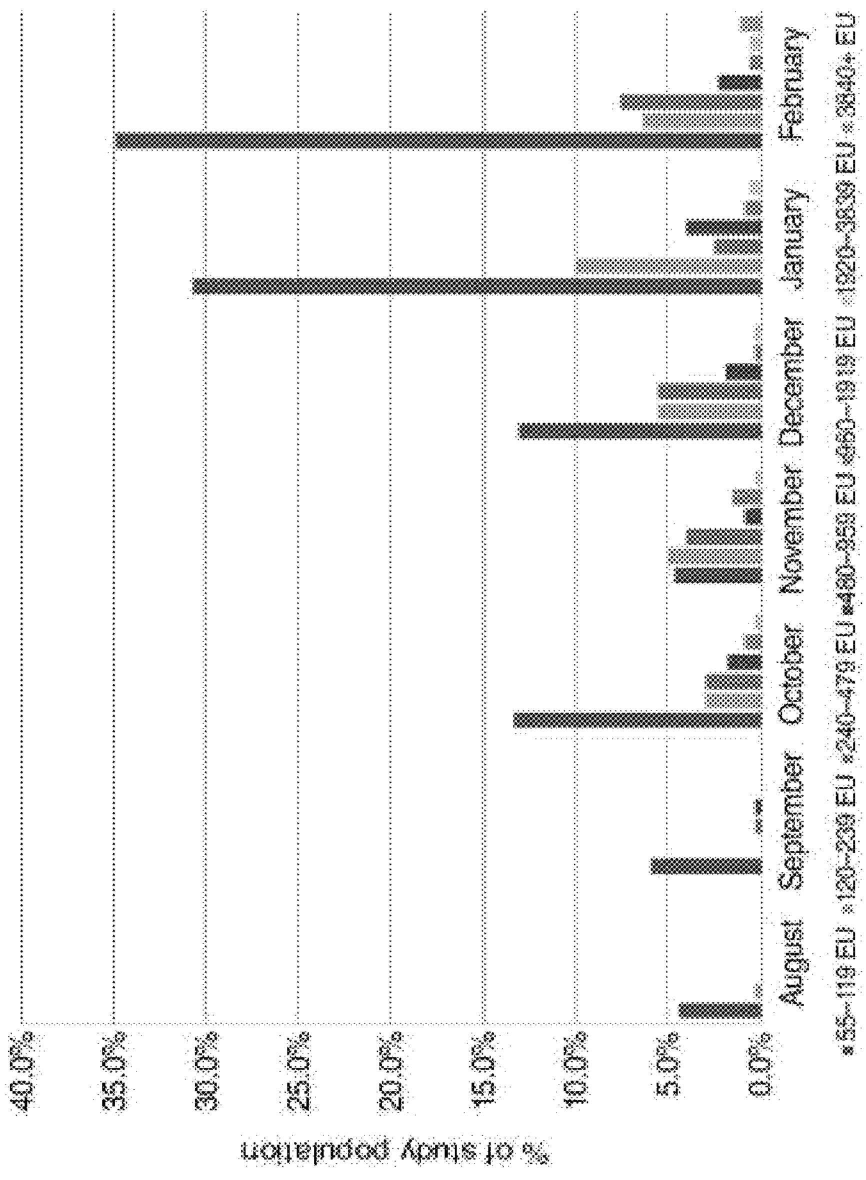
FIG. 4 is a chart depicting monthly distribution of positive enzyme-linked immunosorbent assay (ELISA) results reported as ranges of ELISA units (EU).

ELISA = enzyme-linked immunosorbent assay.

with marked increases in seroconversion during the months of October 2010 and January 2011. As shown in FIG. 4, the majority of the seropositive animals for a given month had EU values in the range of 55-119 EU. Beginning in October, there was an increase in the frequency of high titers (≥120 EU) paralleling the increase in seroconversions noted in FIG. 3.

Serological results from individual farms including past EPE status of the farm, EPE status during the study period and calculated seroprevalence for *L. intracellularis* are shown in Table 1 below.

Figure 5:
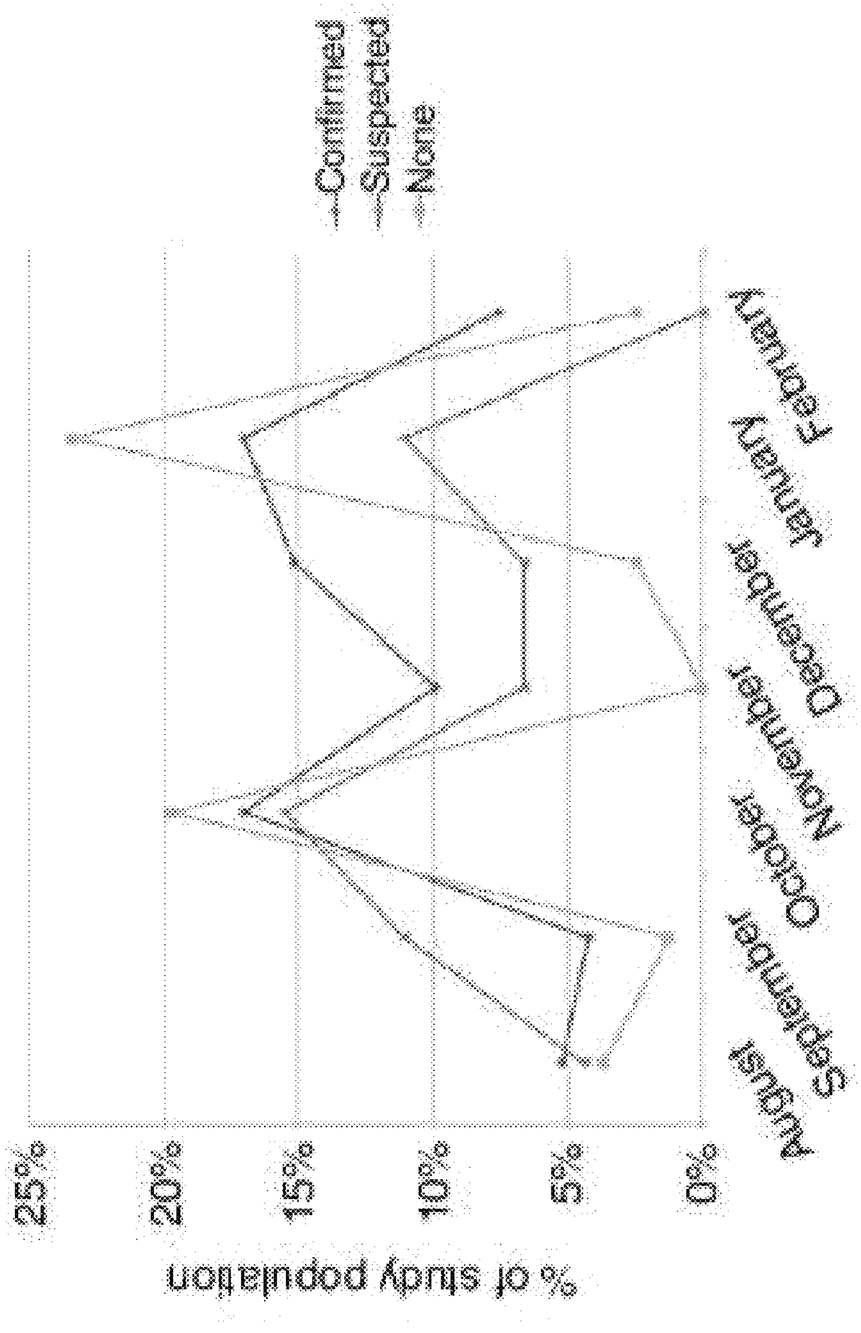
FIG. 5 is a plot showing monthly seroconversions for groups (confirmed, suspected, none) of farms based on recent equine proliferative enteropathy (EPE) history.

A total of 8 farms had confirmed cases of EPE during the study period and no farms had suspected but unconfirmed cases. Seven of these farms had already been classified as having previously confirmed cases of EPE and one had previously had suspected cases of EPE. Farms without a recent history of EPE had no cases during the study period. Calculated farm-specific seroprevalences ranged from 14.3% to 100%. FIG. 5 shows the monthly seroconversion rate grouped by recent EPE history. Whereas those farms with a recent history of EPE (confirmed and suspected) had some horses seroconvert each month, the farms with no recent history of EPE (none) experienced several months in which zero or one horse seroconverted. Table 2 shows the overall average seroprevalence as well as the average positive and maximum titer values obtained from farms grouped by recent EPE status.

TABLE 2

Average seroprevalence, positive enzyme-linked immunosorbent assay (ELISA) units (EU) and maximum EU grouped by equine proliferative enteropathy (EPE) history

| Previous EPE cases | Average seroprevalence | Average positive EU | Average max EU |
|---|---|---|---|
| Confirmed | 76.3%* (55.6-100%) | 228.1 (85.5-378.9) | 1683.4 (193.8-4312.3) |
| Suspected | 55.6% (20-86.7%) | 218.0 (59.7-326.2) | 1604.6 (62.2-3319.4) |
| None | 53.1% (14.3-73.3%) | 123.9** (59.5-175.6) | 453.9*** (55.6-904.1) |

*$P < 0.05$,
**$P < 0.079$,
***$P < 0.056$.

Those farms with a confirmed history of EPE had significantly (P<0.001) higher average seroprevalences compared with those with suspected or no recent cases of EPE. Additionally, the average EU (P=0.079) and average maximum EU values (P=0.056) were found to be lower on farms with no recent history of EPE cases compared with the other groups. Moreover, the range of maximum titers is much smaller for the farms with no recent EPE cases.

Discussion

An ELISA method was used to characterize the serological response of Thoroughbred weanlings to *L. intracellularis* on central Kentucky farms. This ELISA method used column chromatography purified *L. intracellularis*, thus optimizing reproducibility, as evidenced by an overall intra-assay CV of 6.73 and inter-assay CV of 9.60. Using this method, farm-specific seroprevalences ranged from 14.3 to 100%. As such, these results are comparable with a past screening study in the central Kentucky region that used the IPMA method and showed an EPE endemic farm to have a seroprevalence of approximately 60% while a nonendemic farm had a seroprevalence of 17% (Page et al. 2011b).

Not surprisingly, seroprevalences corresponded well with the past history of EPE cases on the farms. Significant difference between groups based on recent EPE history was seen with respect to average seroprevalence. Additionally, farms with no recent clinical cases of EPE had both lower average EU and average maximum EU values for their positive samples. One possible explanation is that farms with no history of EPE cases probably had lower environmental burdens of *L. intracellularis* resulting in fewer horses being exposed to the bacterium (lower seroprevalence) and less antigenic stimulation per exposure (lower EU values). Evidence for this assertion is provided by the nonendemic farm from the previous study (Page et al. 2011b), which is also represented in the current study (Farm 15). While originally considered nonendemic, the farm has since reported suspected cases of EPE and was re-classified for the purpose of this study. Accordingly, the farm's seroprevalence was found to be 60% with an average positive EU of 326.2 and a maximum EU of 3319.4.

Given that the epidemiology of EPE remains poorly defined, these data begin to indicate that relative burdens of *L. intracellularis* in the environment may explain why certain farms have an endemic problem with EPE.

Monitoring of weanlings by the enrolled farms ultimately identified 8 farms with confirmed cases of EPE during the study period from August 2010 to February 2011. Perhaps not surprisingly these 8 farms represented only those with prior confirmed or suspected cases of EPE (7 and 1, respectively). While definitive ante mortem diagnosis of EPE remains controversial, elevated *L. intracellularis*-specific antibody levels are commonly identified in clinically affected horses (Frazer 2008; Page et al. 2011b). These confirmed cases likewise exhibited an increased antibody response, as was also detected in the *L. intracellularis*-challenged weanlings (Page et al. 2011a), using this ELISA. While previous reports from the central Kentucky region suggest a single peak of exposure occurring during late fall/early winter (Frazer 2008; Page et al. 2011b), new evidence shows bimodal exposure occurring both in the fall and winter. These results correspond directly with anecdotal evidence indicating a large increase in the number of cases of EPE in this area during the months of January and February 2011. The reason for this increased incidence of EPE has yet to be elucidated. Possible explanations include changes in weather patterns, changes in management and increased exposure to the unknown reservoir, which could include clinically or subclinically affected horses. With respect to these possibilities, it should be noted that the summer and fall of 2010 experienced less rainfall when compared with average amounts for the region. Additionally, there were lower daily temperatures starting in November with increased amounts of both rain and snow, beyond what is normal for central Kentucky during the early winter months.

While the ELISA method affords ease of use and reliability, the establishment of a cut-off value to separate negative and positive samples is critical. The current positive cut-off (≥55 EU) utilized the average EU plus 3 s.d. from values obtained for nonchallenged weanlings, reported elsewhere (Page et al. 2011a), and differentiated between known seropositve and seronegative horses. Twelve field cases evaluated using the ELISA had high levels of *L. intracellularis*-specific antibodies, equalling or surpassing those EU detected in the experimentally challenged weanlings. Also noted were several nonclinically affected weanlings with markedly elevated EU values. These could be indicative of a successful immunological response to infection or a subclinical case that was not detected by the farm; both situations were observed in the previous challenge study (Page et al. 2011a). As such, these findings provide further evidence that the new ELISA successfully detects antibodies to *L. intracellularis* in clinical and nonclinically affected horses.

There were 2 inherent limitations with the design of this study. First, there was an overrepresentation of farms with confirmed or suspected cases of EPE in the data set. This likely reflected the fact that those farms with a prior history of what they consider to be a frustrating disease were more willing to participate and provide data. Additionally, the stigma associated with this disease in central Kentucky may have contributed to the large number of farms that declined to participate due to fears that their status with respect to *L. intracellularis* and EPE would become public. As such, the overall seroprevalence of 68% should not be considered representative of the equine population in this region without further, randomised sampling. Nevertheless, 20% of the horses surveyed came from farms with no recent history of EPE and we reported both farm-specific and group-specific seroprevalences. The other limitation and potential source for error revolves around the possibility of cross-reaction of this ELISA with other bacteria. Phylogenetic studies have found that while *L. intracellularis* appears to be a member of unique pathogens (Dale et al. 1998), more recent work has shown *L. intracellularis* shares similarities with some rickettsial families (Schmitz-Esser et al. 2008). As such, potential cross-reactivity between other organisms cannot be excluded without further testing. However, work to validate the ELISA from which the method reported here was adapted failed to detect any cross-reactivity between *L. intracellularis* and related bacterial species (Wattanaphansak et al. 2008).

By screening a large population of central Kentucky Thoroughbreds using a newly validated and equine-adapted ELISA, a high seroprevalence for *L. intracellularis*-specific antibodies was detected with variable farm-specific seroprevalences. Previous history of EPE on the farms was associated with significant differences in average seroprevalence indicating lower levels of exposure are present on farms with no history of EPE. Additionally, a bimodal, seasonal distribution of exposure was documented. The high farm-specific seroprevalences and bimodal distribution of exposure to *L. intracellularis* were unexpected and suggest that farms with a previous history of EPE remain at risk due to heightened exposure levels beyond early winter, as has been suggested previously.

It will now be clear to one of ordinary skill in the art that the present method and system have features and advantages over prior techniques including sensitivity and specificity. Variations to the specific process conditions and experimental conditions described herein may be modified or substituted as appropriate and understood by one of ordinary skill in the art, consistent with the present disclosure. This includes modification of the ELISA procedure to incorporate other species-specific reagents such that the ELISA can test samples originating from a variety of other species including, but not limited to, swine, hamsters, rabbits, mice, rats, non-human primates, human, raccoons, birds and insects.

REFERENCES

Numerous references have been cited throughout this disclosure including those listed below, all of which are incorporated by reference.

Boesen, H. T., Jensen, T. K., Brees, D. J., Sondhoff, A. H., Kluge, J. P., Andreasen, C. B. and Brown, C. M. (2005) Evaluation of a novel enzyme-linked immunosorbent assay for serological diagnosis of porcine proliferative enteropathy. Vet. Microbiol. 109, 105-112.

Brees, D. J., Sondhoff, A. H., Cooper, D. M., Swanson, D. L. and Gebhart, C. J. (1999) *Lawsonia intracellularis*-like organism infection in a miniature foal. J. Am. vet. med. Ass. 215, 511-514, 483.

Cooper, D. M., Swanson, D. L., Dale, C. J., Moses, E. K., Ong, C. C., Morrow, C. J., Reed, M. B., Hasse, D., Strugnell, R. A. (1997) Diagnosis of proliferative enteritis in frozen and formalin-fixed, paraffin-embedded tissues from a hamster, horse, deer and ostrich using a *Lawsonia intracellularis*-specific multiplex PCR assay. Vet. Microbiol. 54, 47-62.

Dale, C. J., Moses, E. K. (1998) Identification and sequencing of the groE operon and flanking genes of *Lawsonia intracellularis*: use in phylogeny. Microbiol. 144, (Pt 8), 2073-2084.

Drolet, R., Larochelle, D. et al. (1996) Proliferative enteritis associated with *Lawsonia intracellularis* (ileal symbiont *intracellularis*) in white-tailed deer. J. vet. Diag. Invest. 8, 250-253.

Frank, N., Fishman, C. E. et al. (1998) *Lawsonia intracellularis* proliferative enteropathy in a weanling foal. Equine vet. J. 30, 549-552.

Frazer, M. L. (2008) *Lawsonia intracellularis* infection in horses: 2005-2007. J. vet. Intern. Med. 22, 1243-1248.

Guedes, R. M., Gebhart, C. J., Guedes, R. M., Gebhart, C. J., Deen, J. and Winkelman, N. L. (2002a) Serologic follow-up of a repopulated swine herd after an outbreak of proliferative hemorrhagic enteropathy. Can. J. vet. Res. 66, 258-263.

Guedes, R. M., Gebhart, C. J., Herbst, W., Hertrampf, B., Schmitt, T., Weiss, R. and Baljer, G. (2002b) Validation of an immunoperoxidase monolayer assay as a serologic test for porcine proliferative enteropathy. J. vet. Diag. Invest. 14, 528-530.

Herbst, W., Hertrampf, B. et al. (2003) [Diagnosis of *Lawsonia intracellularis* using the polymerase chain reaction (PCR) in pigs with and without diarrhea and other animal species]. Dtsch. Tierarztl. Wochenschr. 110, 361-364.

Hotchkiss, C. E., Shames, B., Jacobson, M., Aspan, A., Konigsson, M. H., Segerstad, C. H., Wallgren, P., Fellstrom, C., Jensen-Waern, M., Gunnarson, A. (1996) Proliferative enteropathy of rabbits: the intracellular Campylobacter-like organism is closely related to *Lawsonia intracellularis*. Lab. anim. Sci. 46, 623-627.

Jacobson, M., Aspan, A., Jones, G. F., Ward, G. E., Murtaugh, M. P., Lin, G. and Gebhart, C. J. (2004) Routine diagnostics of *Lawsonia intracellularis* performed by PCR, serological and post mortem examination, with special emphasis on sample preparation methods for PCR. Vet. Microbiol. 102, 189-201.

Jones, G. F., Ward, G. E., Kroll, J. J., Eichmeyer, M. A., Schaeffer, M. L., McOrist, S., Harris, D. L., Roof, M. B. (1993) Enhanced detection of intracellular organism of swine proliferative enteritis, ileal symbiont *intracellularis*, in feces by polymerase chain reaction. J. clin. Microbiol. 31, 2611-2615.

Kroll, J. J., Eichmeyer, M. A., Lavoie, J. P., Drolet, R., Parsons, D., Leguillette, R., Sauvageau, R., Shapiro, J., Houle, L., Halle, G., Gebhart, C. J. (2005).

Lipopolysaccharide-based enzyme-linked immunosorbent assay for experimental use in detection of antibodies to *Lawsonia intracellularis* in pigs. Clin. Diagn. Lab. Immunol. 12, 693-699.

Lavoie, J. P., Drolet, R. et al. (2000) Equine proliferative enteropathy: a cause of weight loss, colic, diarrhea and hypoproteinaemia in foals on three breeding farms in Canada. Equine vet. J. 32, 418-425.

Lawson, G. H. and Gebhart, C. J. (2000) Proliferative enteropathy. J. comp. Pathol. 122, 77-100.

Lawson, G. H., McOrist, S. et al. (1993) Intracellular bacteria of porcine proliferative enteropathy: cultivation and maintenance in vitro. J. Clin. Microbiol. 31, 1136-1142.

Page, A. E., Loynachan, A. T., Bryant, U., Stills, H. F., Jr., Adams, A. A., Gebhart, C. J., Pusterla, N. and Horohov, D. W. (2011a) Characterization of the interferon gamma response to *Lawsonia intracellularis* using an equine proliferative enteropathy challenge (EPE) model. Vet. Immunol. Immunopathol. 143, 55-65.

Page, A. E., Slovis, N. M., Gebhart, C. J., Wolfsdorf, K., Mapes, S. M. and Pusterla, N. (2011b) Serial use of serologic assays and fecal PCR assays to aid in identification of subclinical *Lawsonia intracellularis* infection for targeted treatment of Thoroughbred foals and weanlings. J. Am. Vet. Med. Assoc. 238, 1482-1489.

Page, A. E., Stills, H. F., Chander, Y., Gebhart, C. J., Horohov, D. W. (2011) Adaptation and validation of a bacteria-specific enzyme-linked immunosorbent assay for determination of farm-specific *Lawsonia intracellularis* seroprevalence in central Kentucky Thoroughbreds. Equine Veterinary Journal 43 (Suppl. 40) 25-31.

Pusterla, N., Higgins, J. C. et al. (2008a) Epidemiological survey on farms with documented occurrence of equine proliferative enteropathy due to *Lawsonia intracellularis*. Vet. Rec. 163, 156-158.

Pusterla, N., Mapes, S. et al. (2008b) Detection of *Lawsonia intracellularis* by real-time PCR in the feces of free-living animals from equine farms with documented occurrence of equine proliferative enteropathy. J. Wildl. Dis. 44, 992-998.

Schmitz-Esser, S., Haferkamp, I. et al. (2008) *Lawsonia intracellularis* contains a gene encoding a functional rickettsia-like ATP/ADP translocase for host exploitation. J. Bacteriol. 190, 5746-5752.

Schumacher, J., Rolsma, M. et al. (2000) Surgical and medical treatment of an Arabian filly with proliferative enteropathy caused by *Lawsonia intracellularis*. J. vet. Intern. Med. 14, 630-632.

Sorensen, K. and Brodbeck, U. (1986) Assessment of coating-efficiency in ELISA plates by direct protein determination. J. Immunol. Methods 95, 291-293.

Watarai, M., Yamato, Y. et al. (2004) Enzyme-linked immunosorbent assay to detect *Lawsonia intracellularis* in rabbits with proliferative enteropathy. J. vet. med. Sci. 66, 735-737.

Wattanaphansak, S., Asawakarn, T. et al. (2008) Development and validation of an enzyme-linked immunosorbent assay for the diagnosis of porcine proliferative enteropathy. J. vet. Diagn. Invest. 20, 170-177.

Williams, N. M., Harrison, L. R. et al. (1996) Proliferative enteropathy in a foal caused by *Lawsonia intracellularis*-like bacterium. J. vet. Diagn. Invest. 8, 254-256.

The invention claimed is:

1. A method for testing an exposure to a *Lawsonia intracellularis* in a subject, said method comprising:

purifying whole *Lawsonia intracellularis* from host cells and host debris using ion-exchange chromatography on whole intact *L. intracellularis* produced in or on a suitable medium, wherein purifying whole *L. intracellularis* comprises purifying whole *L. intracellularis* cells first using centrifugation prior to the ion-exchange chromatography; and adhering the purified *L. intracellularis* on a suitable material to form an antigen substrate, said substrate adapted for determining whether a subject produces *L. intracellularis*-specific antibodies against the antigen, and thereby for indicating *L. intracellularis* exposure or infection in the subject.

2. The method of claim 1, further comprises growing the *L. intracellularis* in or on the suitable medium.

3. The method of claim 1, wherein the ion-exchange chromatography is diethylaminothyl cellulose (DEAE) chromatography.

4. The method of claim 1, wherein the suitable material is an enzyme-linked immunosorbent assay (ELISA) plate.

5. The method of claim 1, further comprising introducing a serum sample from a subject to the antigen substrate to determine whether the serum contains *L. intracellularis*-specific antibodies against the antigen.

6. The method of claim 4, further comprising centrifuging a blood sample from the subject to produce the serum.

7. A method for diagnosing a *L. intracellularis* infection or exposure in a subject, said method comprising:

acquiring a serum sample from a subject;

introducing the serum sample to an antigen substrate comprising purified *L. intracellularis*, produced from host cells and host debris using ion-exchange chromatography on whole *L. intracellularis*, adhered to a suitable material, wherein the purified *L. intracellularis* are whole *L. intracellularis* whole cells produced by first centrifugation of *L. intracellularis* host cells and pathogen host debris prior to the ion-exchange; and detecting a presence of *L. intracellularis*-specific antibodies in the serum against the antigen substrate bound to the antigen substrate, thereby indicating a *L. intracellularis* exposure or infection in the subject.

8. The method of claim 7, wherein acquiring the serum sample comprises centrifuging a blood sample from the subject to produce the serum.

9. The method of claim 7, wherein the ion-exchange chromatography comprises DEAE chromatography.

* * * * *